United States Patent [19]

Kaplan et al.

[11] Patent Number: 5,272,346

[45] Date of Patent: Dec. 21, 1993

[54] ULTRAVIOLET SPECTROGRAPHIC MONITORING OF WATER SOLUBLE CORROSION INHIBITORS

[75] Inventors: Roy I. Kaplan, Missouri City; J. Byron Strickland, Bellaire, both of Tex.

[73] Assignee: Nalco Chemical Company, Naperville, Ill.

[21] Appl. No.: 866,197

[22] Filed: Apr. 9, 1992

[51] Int. Cl.$^5$ .................. G01N 21/33; E21B 41/02
[52] U.S. Cl. .................. 250/373; 166/902
[58] Field of Search ........... 250/373; 166/902, 310, 166/250

[56] References Cited

U.S. PATENT DOCUMENTS 4,665,981  5/1987  Hayatdavoudi ............... 166/250
5,152,177  10/1992  Buck et al. ................... 73/61.54

FOREIGN PATENT DOCUMENTS 50-80190  6/1975  Japan ........................... 250/373
55-24671  2/1980  Japan ........................... 250/373

OTHER PUBLICATIONS

*The Nalco Water Handbook*, 2nd Edition, Nalco Chemical Company, 1988, pp. 43.1-43.23: Chapter 43, "Oil Field Water Technology".

J. A. Martin and F. W. Valone, "Spectroscopic Techniques for Quality Assurance of Oil Field Corrosion Inhibitors". *Corrosion NACE*, vol. 41, No. 8 (Aug. 1985) pp. 465-473.

J. A. Martin and F. W. Malone, "The Existence of Imidazoline Corrosion Inhibitors." *Corrosion NACE*, vol. 41, No. 5 (May 1985) pp. 281-287.

*Primary Examiner*—Constantine Hannaher
*Attorney, Agent, or Firm*—Joan I. Norek; Robert A. Miller; Joseph B. Barrett

[57] ABSTRACT

The concentration of a water soluble corrosion inhibitor formulation in the water of an aqueous system is monitored by a UV absorption method which is based upon the measurement of the absorbance of a component of corrosion inhibitor formulation. The method is particularly suited to on-site determinations of inhibitor residuals in large aqueous systems, such as in oil field applications, which have an acute need for rapid and adaptable assays, so as to provide precise information before corrosion damage can occur.

20 Claims, 4 Drawing Sheets

Standard Curve; Corrosion Inhibitor Formulation in Wellhead Water Medium; 270 nm; Deionized Water Reference; 50mm Cells

ULTRAVIOLET SPECTROGRAPHIC MONITORING OF WATER SOLUBLE CORROSION INHIBITORS

TECHNICAL FIELD OF THE INVENTION

The present invention is in the technical field of monitoring and controlling the concentration of water soluble corrosion inhibitors, particularly in large aqueous systems.

BACKGROUND OF THE INVENTION

Corrosion of processed metals, such as steel, copper, and zinc, is a process whereby elemental metals, in the presence of water and oxygen, are converted to oxides. Although corrosion is a complicated process, it may be considered an electrochemical reaction involving three steps which occur at the anodic and cathodic sites of a metal surface, as follows:
1. Loss of metal to the water solution in oxidized cationic form at an anodic site, with concomitant release of electrons ("anodic reaction");
2. The flow of the released electrons to a cathodic site: and
3. Oxygen at a cathodic site uses the electrons to form hydroxyl ions ("cathodic" reaction), which flow to an anodic site.

These basic steps are necessary for corrosion to proceed, and the slowest of the three steps determines the rate of the overall corrosion process.

A corrosion control program usually depends on specific inhibitors to stop the anodic reaction, slow the cathodic reaction, or both. Among the various types of corrosion inhibitors are organic filmers, which act by forming filming layers on metal surfaces to separate the water and metal. These materials form and maintain a barrier between the water and metal phases to prevent corrosion.

In most any system employing corrosion inhibitors, the ability to monitor the concentration of corrosion inhibitor in the system would enable one to better control the dosage of corrosion inhibitor. Active corrosion inhibitor components may be consumed in the inhibition process or lost due to deposit, corrosion and chemical degradation processes and combinations of such phenomena. Monitoring the depletion of an active corrosion inhibitor component, particularly if such monitoring permits the extent of depletion to be quantified, is an indicator of treatment program performance. Moreover, if the monitoring results are obtained rapidly and the active component depletion is precisely determined, the monitoring also permits the corrosion inhibitor dosage to be accurately controlled and quickly corrected when necessary.

The need to monitor corrosion inhibitor concentration in an aqueous system is very acute when the system is a large aqueous system, such as the aqueous systems of oil fields. Petroleum reservoirs can vary in length and width from about one to several miles, and in depth from a few feet to several hundred feet. Petroleum is produced first by penetration of a reservoir by a drill, the natural reservoir pressure forcing oil and gas to the surface. Such primary production continues for a period of a few months or several years. The oil leaving a producing well is a mixture of liquid petroleum, natural gas and formation water. During early primary production, the water fraction may be insignificant. Most production thereafter, however, contains sizable proportions of produced water (up to about 90%), generally either as "free water" (which separates from the liquid petroleum in about 5 minutes) or emulsified water. Such post-primary additional production of oil is accomplished using one or more enhanced recovery methods, such as waterflooding, gas injection, and other processing involving fluid or energy injection for secondary or tertiary oil recovery.

Waterflooding, for instance, involves the injection of water as a uniform barrier through the producing formation from a series of injection wells toward a producing well. Such injection wells may be distributed throughout a reservoir or they may be placed at its periphery. During any enhanced recovery processing, formation water is generally being produced, but in waterflooding processes the amount of flood water used often far exceeds the volume being produced. The produced water, together with supplemental surface water, is also generally processed before its use as injection water, by such methods as filtration, clarification, de-aeration, chemical addition and the like.

Steam and carbon dioxide flooding also use large amounts of water. Steam flooding, for instance, involves either the injection of steam for a time period during which the well is taken out of service, or the introduction of a steam-water mixture through a displacement well, from which site the steam and hot water radiate outward toward peripheral oil wells.

Oil field applications not only involve vast amounts of water, they also employ vast amounts of metal conduits and the like that come into contact with such waters. A flowing oil well is generally constructed of "strings" of concentric vertical pipes called casings, and smaller pipes, usually 2 to 3 inches in diameter, called tubing, through which produced fluid flows. The largest diameter casing (the surface string) typically extends to a depth of from about 200 to about 1500 feet, while the intermediate string may reach a depth of up to 5,000 feet, and a third casing (the oil string) may reach the producing zone. Some producing zones are at depths of 20,000 feet or more. A series of valves and flanges at the wellhead control flow. When the natural reservoir energy subsides, some method of pumping is also employed.

Oil fields thus routinely employ large volumes of water and have an immense surface area of pipes, tubes, and other metal fixtures and components in regular contact with such waters that must be protected from corrosion. The primary corrodents in oil field water systems are carbon dioxide, hydrogen sulfide and oxygen. One reason oxygen is corrosive, even at low temperatures, is its participation in creating differential cells beneath deposits on metal surfaces, which become anodic to adjacent deposit-free areas. Control of oxygen corrosion in oil field water systems requires a conscientious effort to exclude air from all surface tanks and vessels and from the casings of producing wells. When hydrogen sulfide is present, iron sulfide deposits, and these deposits are cathodic to base metal. Severe pitting can occur beneath iron sulfide deposits, and if oxygen intrudes into a sulfide system the rate of corrosion can become uncontrollable. Invariably, corrosion inhibitors used in oil field water are organic film formers.

In wells producing a significant crude phase, a corrosion inhibitor that is oil soluble and only slightly water dispersible is often employed. Such corrosion inhibitor will film metal from the oil phase, providing long-term persistency to the metal surface and thus often requiring only intermittent batch feeding of the corrosion inhibitor to the formation down the tubing or into the annulus. In injection water or other systems where water is a significant phase, however, corrosion inhibitors must be either totally water soluble or highly water dispersible to carry through the surface line and tubing system. These corrosion inhibitors generally are not persistent, and it is necessary to feed them continuously, always maintaining a residual amount in the system. Loss of corrosion inhibitor residuals results in desorption of inhibitor film and loss of protection.

Since maintaining corrosion inhibitor residuals is critical to maintaining protection in injection water systems, and in any system having a predominant or significant water phase, inhibitor residuals are routinely determined in the field to provide close control. The currently used method is a procedure wherein the amine-type compounds present in a water sample are first extracted, and then the concentration of these compounds are determined colorimetrically. This and other known procedures are discussed in more detail below.

It would be highly desirable to provide a method for monitoring water soluble corrosion inhibitor concentration in the waters of injection water systems and other large aqueous systems that is faster than current methods. It would be highly desirable to provide such a monitoring method that provides real-time analysis, detecting any corrosion inhibitor underfeeding in time to permit system changes before real corrosion damage occurs. It would be highly desirable to provide such a monitoring method that is product specific, focussing only the compound of interest, and avoiding interferences from other compounds. It would be highly desirable to provide such a monitoring method that directly analyzes one of the "actives" that provide the corrosion protection, instead of an inert dye or other tracer compound that does not behave chemically similar to the corrosion inhibitor product. It would be highly desirable to provide such a monitoring method that determines corrosion inhibitor actives precisely, while maintaining the desired speed and product specificity. It is an object of the present invention to provide such a method with aforesaid highly desirable advantages over current methods of monitoring corrosion inhibitors, and by virtue of such fast, specific and precise monitoring also provide a method for controlling the dosage of corrosion inhibitor for such systems. The invention and these and other objects and advantages of the invention are described in more detail below.

DISCLOSURE OF THE INVENTION

The present invention provides a method for monitoring the concentration of a water soluble corrosion inhibitor formulation in the water of an aqueous system, which comprises the use of a scanning spectrophotometer to scan the absorbance of the sample along at least a segment of the ultraviolet wavelength range, measuring the absorbance value of the sample at a selected absorbance peak, and then determining the concentration by comparing the absorbance value of the sample to a standard curve. The present invention also provides such a method that includes the further step of adjusting the dosage of corrosion inhibitor in the aqueous system in view of the results of the concentration determination. The present invention provides methods for monitoring the concentration of a water soluble corrosion inhibitor formulation in aqueous systems and for controlling the dosage of a water soluble corrosion formulation in aqueous systems, as more fully described below.

PREFERRED EMBODIMENTS OF THE INVENTION

Figure 1:
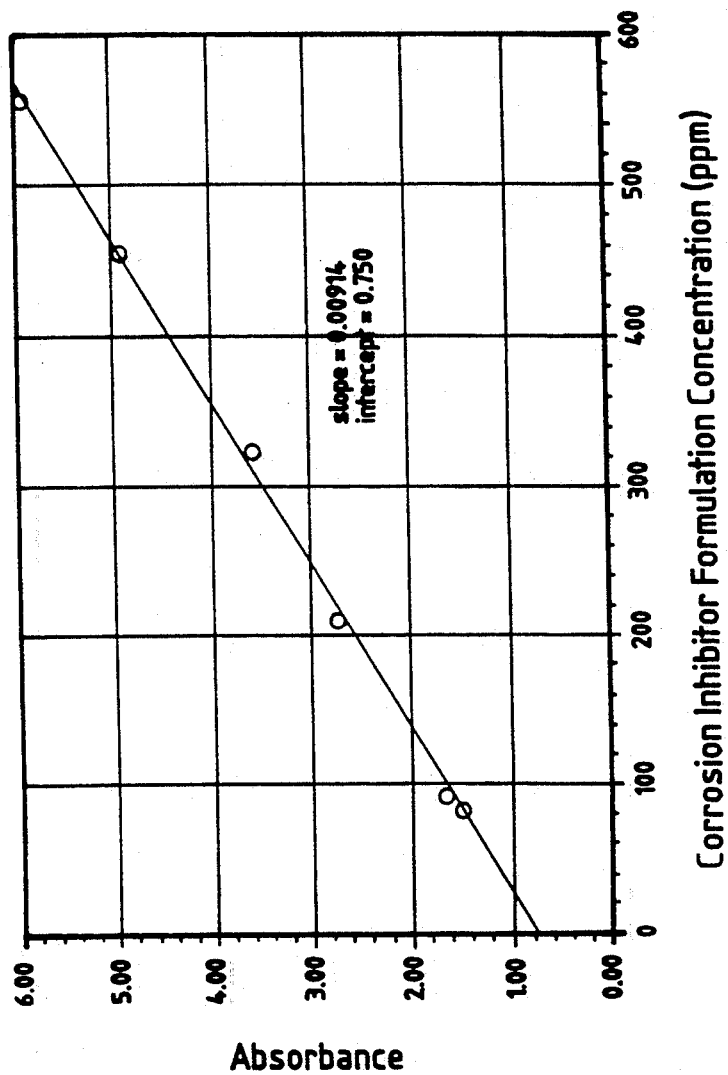
FIG. 1 is a standard curve for a water soluble corrosion inhibitor formulation in an aqueous medium.

The corrosion inhibitors used in oil field water are organic film formers that absorb onto metal surfaces to shield the metal from corrodents. As noted above, the corrosion inhibitors employed in systems having a significant or predominant water phase are routinely water soluble corrosion inhibitors that film from the water phase, rather than the oil phase, and hence form dynamic, rather than persistent, films. It is essential for corrosion protection that an amount of corrosion inhibitor residuals be maintained in the water of the system at all locations. Such water soluble corrosion inhibitors are routinely added downhole on a continuous basis, and at times as intermittent "slugs" of corrosion inhibitor at higher than normal dosage. Monitoring of such corrosion inhibitors to assure the presence of an adequate concentration of corrosion inhibitor residuals in the produced waters, and adjusting the system when the necessity therefor is indicated by the monitoring results, is a very important aspect of corrosion control programs.

A typical water soluble corrosion inhibitor formulation may contain, as the filming component, such known corrosion inhibitors as imidazoline and pyridine derivatives. Since such components must at minimum be water soluble, or at least water dispersible, at their use concentrations, such inhibitor species are generally employed as their various salt species, such as acid-amine salts or quaternary ammonium salts ("quats" or "quaternary salts"). The corrosion inhibitor formulation may also contain other actives, such as surfactants, and inert water soluble or water miscible diluents or solvents. The analysis of imidazoline-type oil field corrosion inhibitors by carbon-13 nuclear magnetic resonance and Fourier transform-infrared spectroscopy is discussed in "Spectroscopic Techniques for Quality Assurance of Oil Field Corrosion Inhibitors," J. A. Martin and F. W. Valone, *Corrosion*, V. 41, No. 8, August 1985, p. 465–473, incorporated hereinto by reference. Such spectroscopic methods, plus ultraviolet spectroscopy, for the investigation of this type of oil field corrosion inhibitor is discussed in "The Existence of Imidazoline Corrosion Inhibitors," J. A. Martin and F. W. Valone, *Corrosion*, V. 41, No. 5, May 1985, p. 281–287, incorporated hereinto by reference. The latter paper in particular discusses a spontaneous hydrolysis of imidazoline to its amide precursor, verified by $^{13}$C NMR, Fourier transform-infrared (FT-IR), and UV. The UV study qualitatively followed the hydrolysis reaction by observing changes in the relative intensitites of the UV absorptions of the amide (approximately 207 nm) and the imidazoline (approximately 232 nm), and determined that the imidazoline/amide ratio decreases with time. In that study, the normal aromatic solvent was replaced with a spectral grade methanol solvent to avoid solvent absorption overlap with the amide and imidazoline absorptions. A correction by subtracting the absorption due to the dimer-trimer acid from that measured for the formulated corrosion inhibitor was also required. The spectrographic techniques discussed in these papers are neither intended nor suitable for field assays.

The extraction field method for determining corrosion inhibitor residuals does not distinguish one compound from another, when a plurality of extractable compounds are present in the water sample. The extraction field method may require a time period of from about 45 to about 60 minutes or longer from sampling to assay results. The method of the present invention is much faster than the extraction method, and hence permits a rapid response to changes in the concentration of residuals.

The compound being determined by the present invention, moreover, is the active filming corrosion inhibitor component, or one of a plurality of such components. Thus the monitoring ability provided by the present invention is far more realistic and reliable than the use of inert tracers, which may be added together with a corrosion inhibitor formulation. For instance, in the absence of any substantial corrosion inhibitor loss due to deposit, degradation and the like, depletion of corrosion inhibitor concentration is mainly due to performance consumption. The corollary is that the absence of inhibitor depletion to the extent expected could indicate overdosage of inhibitor, or failure of an inhibitor's performance. An inert tracer, which of course is not involved in the active components' chemistries, does not provide the accurate systems information, such as the extent of actives depletion, obtainable by monitoring the inhibitor actives themselves.

The dosage of a formulated corrosion inhibitor, including all actives and inert diluents and/or solvents, is broadly from about 1, or about 5, to about 10,000, or at times 20,000, parts per million based on weight ("ppm"). Within such broad range, it is common to find a formulated corrosion inhibitor being dosed in an amount within the narrower range of from about 10 to about 500 ppm. The higher dosage levels of either range generally represent slug dosages of the formulation. The concentration of corrosion inhibitor residuals in, for instance, produced waters of an oil field employing a substantially continuous addition of water soluble corrosion inhibitor is often on the order of from about 10, or 20, to about 150, or 200, ppm when the residuals level is adequate, and of course would be lower if an undesirable fall-off of residuals occurred. A field monitoring method must be applicable to a relatively broad range of concentrations, and in particular concentrations of low levels close to the boundary between sufficient and inadequate inhibitor residuals. A field monitoring method should preferably also accurately determine higher concentrations, so that the residuals monitoring can be continued without procedural modifications despite intermittent sluggings of the system. The present method is applicable to such broad ranges in concentrations.

As noted above, the currently used extraction procedures for monitoring the concentration of residual corrosion inhibitor is not as responsive as desired for use as an early warning system. The method of the present invention provides a procedure that is about 10 times faster than the extraction method. The delay between sampling and assay results is only about 10 minutes, which permits, when necessary, system changes to be made based on such results before any real corrosion damage can occur.

Large flowing aqueous systems, such as oil well fields, require a field method that quickly and accurately measures the corrosion inhibitor concentration levels in its water, from initial injection, through production, until final produced water reinjection, to assure adequate corrosion protection for its water system. The present method may be employed to determine corrosion inhibitor residuals in free water samples from any source point. The term "free water" as understood in the art, and as used herein, means water that is neither emulsified in oil nor entrained in a gas. The present method is thus applicable to numerous pipeline applications.

The sample preparation for a field assay method preferably should be simple and the analytical method rapid and adaptable. The present method provides both a simple sample preparation and a rapid, adaptable analytical method. The present method has been demonstrated to be quick, easy and reproducible.

The present method determines the concentration of a formulated corrosion inhibitor by determining the concentration of a component thereof by its absorbance in the ultraviolet wavelength range. In preferred embodiment such component is one of the active corrosion inhibitor components. In more preferred embodiment such component is the, or one of the, filming actives. In more further preferred embodiment, such component is a moderately substituted, water soluble pyridine derivative.

The present method, in one very preferred embodiment, employs ultraviolet spectroscopy using the electronic transition centered at 270 nm (nanometer) arising from an alkyl pyridine quat component of a water soluble corrosion inhibitor. The present method may be employed to quantitatively assess concentration levels of such alkyl pyridine component, and based thereon the concentration of the formulated corrosion inhibitor.

The present method may be used, as noted above, to relate the absorbance of a component to the concentration of formulated corrosion inhibitor, and this determination may be made without any knowledge concerning the concentration of that, or other, components in the formulated product. Thus the present method may advantageously be employed regardless of whether or not specific formulation information is available.

Sample Preparation

If a water sample is contaminated with oil, the oil can and should be removed before analysis without the use of demulsifiers. Centrifugation or heat treatment (up to 150° F.), followed by a simple mechanical oil-water separation technique, such as decantation, should be sufficient to remove the major fraction of the oil contaminant. Any remaining oil residuals or solids are removed by filtering the sample through a 0.45 micrometer Millipore cellulose acetate filter. When the component being determined is a filming component, loss through such a compound's propensity to film onto most any surface encountered should be minimized. Therefore syringe filters are preferably employed for such filtration and only a 20 ml volume of the water sample is employed for the assay. After such filtration, the aliquot should have a visually clear appearance. Sample color has not been found to interfere with the analysis, and thus color removal is not generally necessary.

Ultraviolet Analysis

A filtered water sample is added to one of a matched set of 50 mm VWR "SPECTROSIL" far UV quartz spectrophotometric cells, preferably washing the cell twice with small amounts of the sample prior to filling and stoppering. The second cell of the set is used as the reference cell, and it is filled with deionized water (the reference solvent). A scanning spectrophotometer, such as a Cary Model 1 scanning spectrophotometer, is then used to span the relevant spectral region (which is from 200 nm to 300 nm for the type of component used in the following examples). The absorption of the component in question, at the desired absorption peak, which is generally the component's major UV absorption peak, is determined using the computer's cursor. This absorption peak is at 270 nm (extinction coefficient maximum of about 8400) for the component used is the following examples. Then the concentration equivalent of the formulated corrosion inhibitor, in convenient parameter, such as ppm, is determined from a standard curve.

Standard Curve Preparation

Since produced waters and the like alone may exhibit absorption peaks in the region of interest, it may be preferable at times to prepare a specific standard curve for a given field site using, as the aqueous medium, representative produced waters from that site. Such representative produced waters should not contain any corrosion inhibitor. Standards containing a known concentration of the formulated corrosion inhibitor in such medium are prepared at concentrations preferably spanning the concentration levels expected to be encountered in actual corrosion inhibitor-containing water at the given site. Twenty ml of each standard concentration sample is then filtered through a 0.45 micron Millipore syringe filter as a simulation of the field sample preparation procedure. The analysis method described above is then employed to determine the absorbance about the wavelength chosen for each concentration level. This data is plotted (concentration versus absorbance) to provide a standard curve. In the alternative, one might prepare a standard curve applicable to a plurality of sites, using deionized water as the medium, and then for each site determine the contribution to absorbance provided by the background of the produced waters. The plotted absorbance values would then be the absorbance values determined for the field samples, corrected by subtracting therefrom the absorbance contribution of the background. Another alternative is to use a prepared aqueous medium that simulates the composition of the background that will be encountered in field assays.

The Formulated Corrosion Inhibitor

Corrosion inhibitors A and B used in the following Example are both commercial corrosion inhibitor products available from Nalco Chemical Company, Naperville, Ill. These formulated corrosion inhibitors are widely used for oil field corrosion inhibition. They are water soluble corrosion inhibitors that contain, as a component contributing to filming, an alkyl pyridine quat component, together with an imidazoline type filmer. The dosages of such formulations used in the Examples are representative of commonly used dosage levels.

EXAMPLE 1

Figure 2:
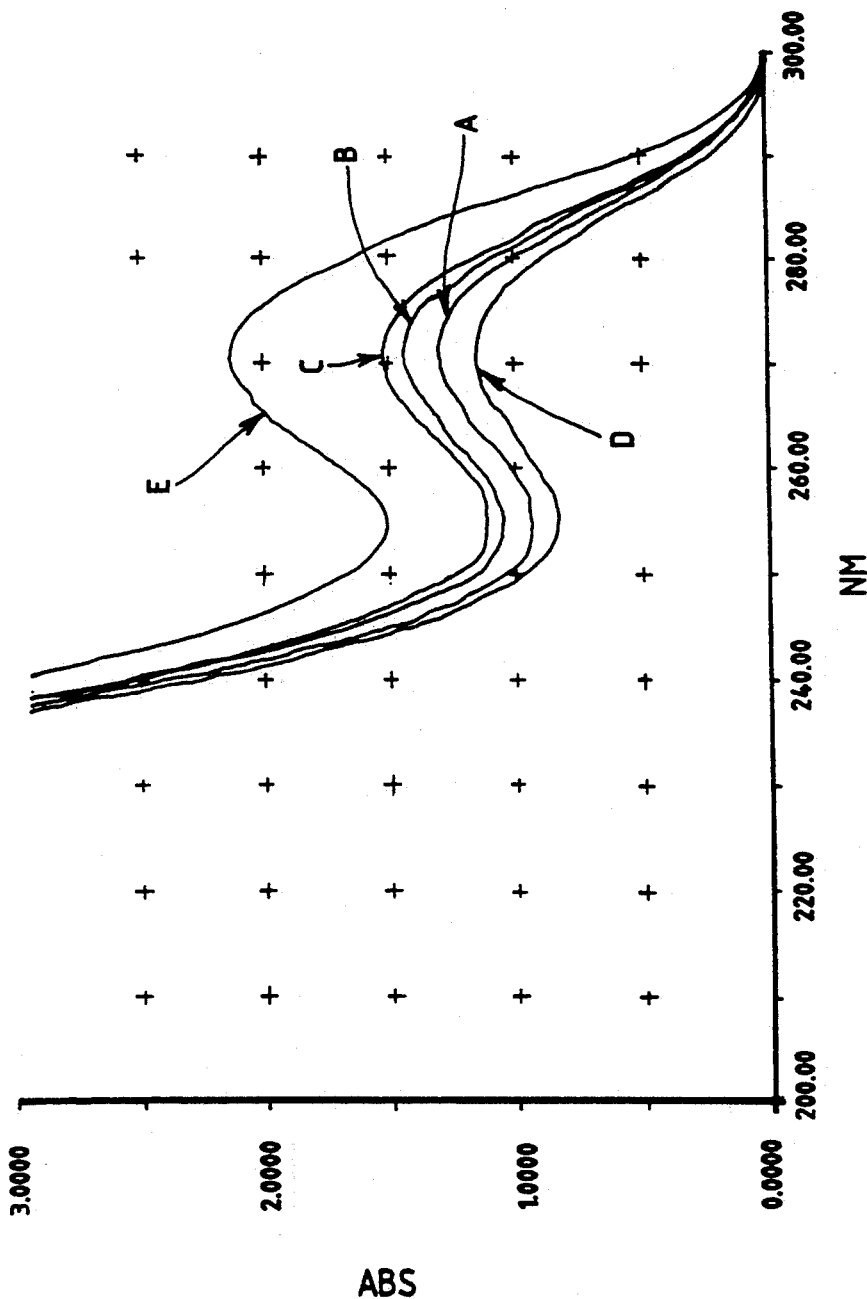
FIG. 2 is an ultraviolet spectra showing the absorbance of a plurality of oil field water samples made the day of sampling.
Figure 3:
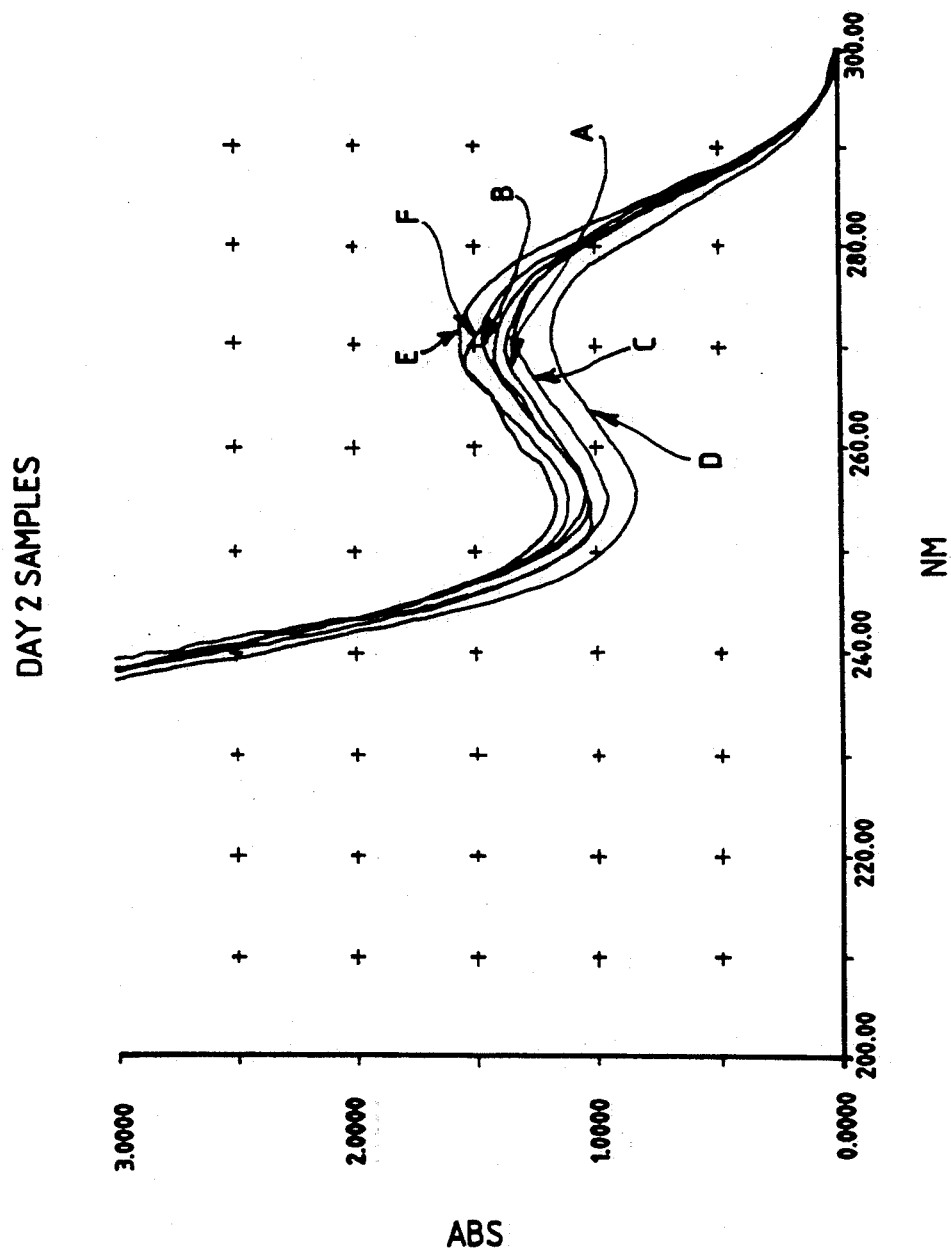
FIG. 3 is an ultraviolet spectra showing the absorbance of a plurality of oil field water samples made a day after sampling.

Wellhead water from a designated well of a commercial oil field was used to prepare a standard curve, using the Standard Curve Preparation method described above, for corrosion inhibitor A, in concentrations ranging from 25 ppm to 550 ppm of formulated corrosion inhibitor A. The resultant standard curve (absorbance versus formulated corrosion inhibitor A concentration) is shown in FIG. 1 and this curve is linear through the concentration range employed. As indicated on FIG. 1, the standard curve has a slope 0.00914 and intercept of 0.750. Then water samples from the produced water system leading to a certain flow station at such oil field were taken on several days, and the concentrations of the formulated corrosion inhibitor therein were determined on the sampling day, in the field, using the method described above and the standard curve of FIG. 1. The concentration values determined on the sampling date were substantially reproduced one day later and again about two weeks later in an off-field research laboratory. During the time periods between assays the samples were stored in closed glass sample bottles. The corrosion inhibitor residuals concentrations were in general within the range of from about 43 to about 83 ppm, with excursions up to about 150 ppm during periods of slugging. A Cary Model 1 scanning spectrophotometer was used for both the standard curve preparation and the analysis of the samples and the computer parameters employed are shown below in Table 1. The concentration values determined from the produced water samples are shown below in Table 2. The spectra obtained on days 1 and 2 are shown, respectively, in FIG. 2 and 3.

TABLE 1

| Parameter | Value |
| --- | --- |
| Photometric Mode | Absorbance |
| Abscissa Mode | NM |
| Ordinate (Y) Min/Max | 0.0000/3.0000 |
| Abscissa (X) Min/Max | 200.00/300.00 |
| SBW (nm) | 2 |
| Signal Averaging Time (sec) | 0.033 |
| Data Interval | 0.056 |
| Scan Rate (nm/min.) | 100 |
| Lamps on | UV-Visble |
| Baseline Correct | Off |
| Auto Scale/Auto Store | No/No |

TABLE 2

| Sample Date | Analysis Date | Location Designation | Absorbance at 270 nm | Corrosion Inhibitor Conc. (ppm) | Sample pH |
| --- | --- | --- | --- | --- | --- |
| 1 | 16 | A | 1.298 | 60 | 8.2 |
| 1 | 16 | B | 1.260 | 56 | 8.1 |
| 1 | 16 | C | 1.506 | 83 | 7.7 |
| 1 | 16 | D | 1.146 | 43 | 7.8 |
| 1 | 16 | E | 2.118 | 150 | 8.0 |
| 2 | 16 | A | 1.218 | 72 | 7.9 |
| 2 | 16 | B | 1.208 | 77 | 8.0 |
| 2 | 16 | C | 1.364 | 67 | 8.0 |
| 2 | 16 | D | 1.173 | 46 | 7.5 |
| 2 | 16 | E | 1.561 | 89 | 8.0 |
| 3 | 16 | F | 1.502 | 82 | 7.5 |

EXAMPLE 2

Figure 4:
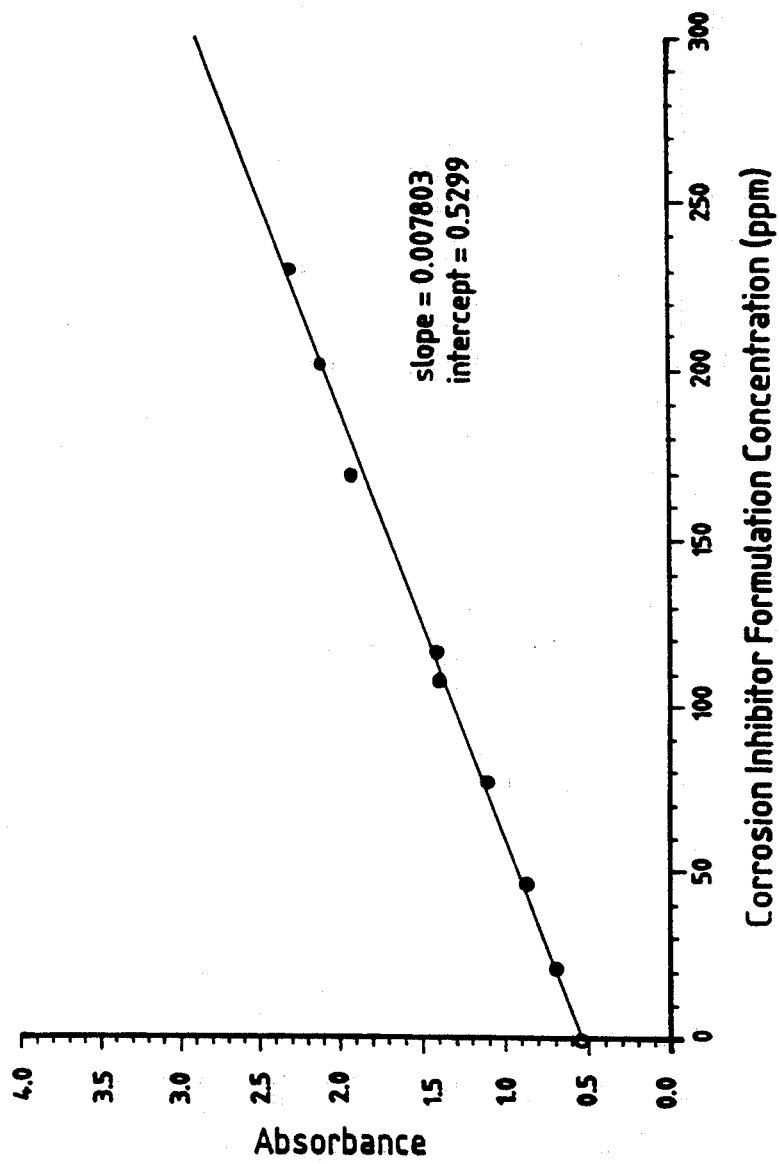
FIG. 4 is a standard curve for a water soluble corrosion inhibitor in an aqueous medium.

Crude oil-water samples, containing no corrosion inhibitor at the time of sample retrieval, were taken from two separate producing wells in an oil field, and were allowed to stand until the oil and water layers separated. The water layers were then filtered twice through 1.65 micron Millipore cellulose acetate filters, and then twice through 0.45 micron membranes to remove dispersed oil, providing clear and colorless water. These produced waters were found to have a broad absorption peak in the area of interest, that is centered in the 265 to 280 nm range, and thus these waters were used as the aqueous medium for the standard solutions to alleviate the background interference caused by such absorption peak. A 50:50 bend by volume of such waters was used for the preparation of a standard curve. The standard solutions prepared using such aqueous medium contained corrosion inhibitor B in concentrations ranging from 0 to 230 ppm. Corrosion inhibitor B, as described above, is a water soluble, formulated corrosion inhibitor. These standard solutions were scanned for absorbance and a standard curve was prepared from the concentration and absorbance values as described in above in the Standard Curve Preparation section. The resultant standard curve is shown in FIG. 4. This standard curve was successfully used to determine the concentration of corrosion inhibitor B in various produced water samples from this oil field, on site, using the Ultraviolet Analysis procedure described above.

EXAMPLE 3

To demonstrate the effect of successive filtrations on concentration values of a corrosion inhibitor formulation determined by the method of the present invention, a laboratory study was conducted using, as the formulated corrosion inhibitor, corrosion inhibitor A, described above. This formulated corrosion inhibitor contains at least one filming component that has a broad absorption peak in the UV region. As shown in Example 1 above, the absorption peak of this filming component was usable for the method of the present invention. Since filmers film onto surfaces encountered, some of that component is lost whenever a fresh surface is encountered. The films produced by such filmers generally are only a single molecule or so thick, and hence there is a limit to the component's depletion from a solution. This Example 3 demonstrates that each successive filtration, which introduces a fresh surface at each instance, diminishes the concentration value of the corrosion inhibitor formulation, as determined by the present method, only slightly. The filters employed for this study were 25 mm diameter, 0.45 micron cellulose acetate syringe filters. The syringes were 60 ml disposable plastic syringes with threaded tips. A standard solution "X" of corrosion inhibitor A was prepared by dissolving 109 milligrams of corrosion inhibitor A in 500 grams of deionized water. Two dilutions of standard solution X were made with deionized water to prepared standard solutions "Y" and "Z", which were aqueous solutions containing respectively 30% and 10% standard solution X. The procedure then followed for each of these standard solutions was:

1. A 50 mm quartz cell was rinsed once with deionized water and then twice with unfiltered standard solution. The cell was then filled with the standard solution. A matched cell was filled with deionized water and used as a reference cell.
2. The cells were placed in the spectrophotometer and the instrument was zeroed at 300 nm. The sample was then scanned from 240 nm to 300 nm.
3. The absorption at 270 nm was then determined from the scan. The absorbance value was corrected by adding 0.750 (because the calibration curve was based on produced water with a background absorbance of 0.750 when no corrosion inhibitor was present), and then the corrected absorbance value was converted to ppm corrosion inhibitor A using the standard curve shown in FIG. 1.
4. A 30 ml aliquot of the standard solution was then drawn through a needle into a syringe.
5. The needle was then replaced by a syringe filter and the solution filtered therethrough with gentle plunger pressure into a clean glass beaker.
6. A test cell was then rinsed once with deionized water and twice with the filtered sample, and then the cell was filled with the filtered sample.
7. The filtered sample was scanned, the absorption at 270 nm was determined, and the concentration of corrosion inhibitor A was determined from the standard curve.
8. The sample in the cell was then recombined with the remainder of the filtered sample in the beaker.
9. Then steps 4 through 8 were repeated several times for the given standard solution to provide corrosion inhibitor A determinations upon successive filtrations.

The results of such determinations, in terms of concentration of corrosion inhibitor A for the standard solutions after from zero to five filtrations are listed below in Table 3, from which it is seen that the amount of the filming component lost upon each filtration was from about 1 to about 1.5 percent of the total. The concentrations used for the standard solutions are representative of the concentrations of residuals obtained in a typical oil field using a continuous corrosion inhibitor treatment. It is believed that the percentage of loss in samples from slug treatments with very high concentrations of residuals would be less because the amount lost is dependent on the area of fresh surface encountered during the filtration, such as the syringe barrel and filter. These results indicate that the loss of a filming component by a single filtration of a water sample is not significant for the purposes of the present invention, but repeated filtrations, or other handling exposing a sample unnecessarily to materials that could accommodate a film of the component, should be avoided.

TABLE 3

| Standard Solution | Number of Filtrations Prior to the Analysis | Concentration of the Corrosion Inhibitor Formulation (ppm) |
|---|---|---|
| X | 0 | 230 |
| X | 1 | 227 |
| X | 2 | 224 |
| X | 3 | 221 |
| X | 4 | 218 |
| X | 5 | 215 |
| Y | 0 | 70 |
| Y | 1 | 68 |
| Y | 2 | 67 |
| Y | 3 | 66 |
| Y | 4 | 65 |
| Y | 5 | 65 |
| Z | 0 | 22 |
| Z | 1 | 22 |
| Z | 2 | 22 |
| Z | 3 | 21 |
| Z | 4 | 22 |

TABLE 3-continued

| Standard Solution | Number of Filtrations Prior to the Analysis | Concentration of the Corrosion Inhibitor Formulation (ppm) |
|---|---|---|
| Z | 5 | 21 |

The method of the present invention in one embodiment is a method for monitoring the concentration of a water soluble corrosion inhibitor formulation in the water of an aqueous system, which comprises:
 (a) placing a sample of the water from the aqueous system in a spectrophotometric cell of a scanning spectrophotometer;
 (b) scanning the absorbance of the sample along at least a segment of the ultraviolet wavelength range against a deionized water reference, wherein the scanned ultraviolet wavelength segment encompasses a wavelength "x";
 (c) measuring the absorbance value of the sample at an absorbance peak centered about the wavelength x; and
 (d) comparing the absorbance value of the sample to a standard curve.

The standard curve, as described above, is a plot of known standard solutions concentrations of the corrosion inhibitor formulation in aqueous medium versus the absorbance values of these standard solutions at an absorbance peak centered about the wavelength x. The selection of a specific wavelength as wavelength x is dependent upon the components of the formulation. The corrosion inhibitor formulation should contain a component that has an absorption peak, and preferably a major absorption peak, substantially centered about the wavelength chosen as wavelength x. The concentration of the formulated corrosion inhibitor in the sample is determined by correspondence of its the absorbance to a concentration on the standard curve.

In another embodiment, the present invention is a method for controlling the concentration of a water soluble corrosion inhibitor in the water of an aqueous system, which comprises:
 (a) placing a sample of the water from the aqueous system in a spectrophotometric cell of a scanning spectrophotometer;
 (b) scanning the absorbance of the sample along at least a segment of the ultraviolet wavelength range against a deionized water reference, wherein the scanned ultraviolet wavelength segment encompasses a wavelength x;
 (c) measuring the absorbance value of the sample at an absorbance peak centered about the wavelength x;
 (d) comparing the absorbance value of the sample to a standard curve; and
 (e) adjusting the dosage of the corrosion inhibitor formulation for the aqueous system to provide the desired total concentration of residuals of the corrosion inhibitor formulation in the aqueous system.

The standard curve is as described above. Again the corrosion inhibitor formulation contains a component that has an absorption peak substantially centered about wavelength x, and the concentration of the formulated corrosion inhibitor in the sample is determined by correspondence of its the absorbance to a concentration on the standard curve.

In these methods, the corrosion inhibitor formulation preferably contains an active inhibitor component that has an absorption peak substantially centered at wavelength x. In more preferred embodiment, the corrosion inhibitor formulation contains a water soluble filming pyridine derivative component that has an absorption peak substantially centered at wavelength x. Preferably the water sample is filtered before it is placed in the scanning spectrophotometer to remove any residual oil and/or solids. Minimization of surface area coming into contact with the sample is important if the component that absorbs at wavelength x is a filmer, such as the preferred water soluble filming alkyl pyridine quaternary ammonium salt component.

In these methods the water sample generally contains a sufficient concentration of the formulated corrosion inhibitor so that the component thereof that absorbs at wavelength x can be detected by the methods. Such concentration broadly is from about 1 to about 20,000 ppm of the corrosion inhibitor formulation, and more commonly from about 10 to about 200 ppm of the corrosion inhibitor formulation. The present methods are not, however, limited in use solely for water samples having at least about 1 ppm of formulated corrosion inhibitor, because an assay wherein less than normal, or no, inhibitor is detected would of course provide useful information.

These methods are particularly useful for oil field applications, and the use of these methods for the aqueous systems of oil fields is a preferred embodiment. Moreover, the use of these methods in other large aqueous systems is also a preferred embodiment. Aqueous systems such as oil field systems have a great need for the methods of the present invention, as explained above. Nonetheless there is no reason to limit the use of the present methods to oil field applications, or even large aqueous systems, particularly if there is a need for a rapid and adaptable method for assaying the concentration of a water soluble corrosion inhibitor formulation in such other aqueous systems.

In these methods at times it may be preferable to use inhibitor-free produced waters or the like as the aqueous medium of the standard solutions, so that such aqueous medium has an absorbance at wavelength x substantially commensurate to the background absorbance at wavelength x of the water sample. Another alternative for avoiding background interference when present is to employ deionized water as the aqueous medium of the standard solutions. In such instance, any contribution to the absorbance at wavelength x from the background of the water sample is deducted from the absorbance value of the water sample. This alternative is preferred of course when there is no significant contribution to the absorbance from the background, and hence no need to apply a correction. This alternative also permits standard curves to be prepared for use at multiple sites or for water samples having different backgrounds. Another alternative is to employ a synthetic "background" water as the aqueous medium of the standard solutions, such as a laboratory prepared brine solution that sufficiently matches the brine composition of the water samples.

The present methods may be used for water samples generally regardless of the pH of such samples. An excessively high pH, for instance above 10 or 11, would not normally be encountered in an aqueous system employing water soluble corrosion inhibitors, nor would an extremely low pH, such as below 4, or 3. If extremes in pH are present in a given water system, it is believed that the present methods are usable nonetheless. The present methods may also be used regardless of the temperature of the water samples. Excessively high temperatures, such as temperatures at or close to the boiling point of water, and very low temperatures, such as temperatures at or close to the freezing point of water, would not normally be encountered in an aqueous system employing water soluble corrosion inhibitors. Nonetheless the present methods can be employed even for water samples having such extreme temperatures when sampled without any temperature adjustment other than the normal temperature moderation effect which would occur during the time period of sample preparation at ambient temperatures.

The preferred substituted pyridine derivatives (employed as the component absorbing at wavelength x) should be at minimum moderately active as a filming corrosion inhibitor in the aqueous system in question. Such a pyridine derivative would have a substituent (a radical other than hydrogen) at least one position on the heterocyclic aromatic pyridine ring, which position would normally be the 2-position. Such substituent may be a straight chain or branched alkyl, having from 1 to about 10 carbons, and more typically from 1 to about 8 carbons, and combinations and mixtures thereof, and such alkyl may itself have other substituents, such as halo, hydroxyl, amino, and the like substituents. Such pyridine derivative normally would be employed in salt form, which salt form includes quaternary ammonium salts.

A corrosion inhibitor formulation, or formulated corrosion inhibitor, as these terms are used herein, refers to a composition having one or more components, some of which components may be inert substances, in the sense of having no corrosion inhibiting activity, but at least one of which components is an active corrosion inhibitor. The ultraviolet band or range refers to the band of electromagnetic radiation of the wavelength range from about 185 to about 400 nm, which is radiation having wavelengths shorter than the wavelengths of visible light but longer than those of X rays.

If not expressly indicated otherwise, all percentages or proportions stated herein are based on weight.

Industrial Applicability of the Invention

The present invention is applicable to industries employing water soluble corrosion inhibitors in aqueous system, such as the oil and gas production industries.

We claim:

1. A method for monitoring the concentration of a water soluble corrosion inhibitor formulation in the water of an aqueous system, comprising:
   obtaining a sample of water of an aqueous system to which has been added a water soluble corrosion inhibitor formulation that contains an active corrosion inhibitor component that has an absorption peak substantially centered about a wavelength x;
   optionally removing oil and/or solids from said sample of water by decantation and/or filtration;
   placing said sample of water in a spectrophotometric cell of a scanning spectrophotometer;
   scanning the absorbance of said sample along at least a segment of the ultraviolet wavelength range against a deionized water reference, wherein said scanned ultraviolet wavelength segment encompasses said wavelength x;
   measuring the absorbance value of said sample at an absorbance peak centered about said wavelength x; and
   comparing said absorbance value of said sample to a standard curve comprising a plot of standard solutions having known concentrations of said corrosion inhibitor formulation in aqueous medium versus the absorbance values of said standard solutions at an absorbance peak centered about said wavelength x;
   whereby the concentration of said formulated corrosion inhibitor in said sample is determined by correspondence of its said absorbance to a concentration on said standard curve.

2. The method of claim 1 further including the step of filtering said sample prior to said scanning of said sample.

3. The method of claim 1 wherein said corrosion inhibitor formulation contains a water soluble filming pyridine derivative component that has an absorption peak substantially centered at wavelength x.

4. The method of claim 1 wherein said corrosion inhibitor formulation contains a water soluble filming alkyl pyridine quaternary ammonium salt component that has an absorption peak substantially centered at wavelength x.

5. The method of claim 1 wherein said water sample contains from about 1 to about 20,000 ppm of said corrosion inhibitor formulation.

6. The method of claim 1 wherein said water sample contains from about 10 to about 200 ppm of said corrosion inhibitor formulation.

7. The method of claim 1 wherein said aqueous system is an oil field system in which water is a significant phase.
   wherein said corrosion inhibitor formulation inhibits corrosion by the formation of an inhibitor film on surfaces of said aqueous system, and
   wherein loss of residuals of said corrosion inhibitor formulation in said water of said aqueous system results in the desorption of said inhibitor film.

8. The method of claim 1 wherein said aqueous medium of said standard solutions has an absorbance at wavelength x substantially commensurate to the background absorbance at wavelength x of said water sample.

9. The method of claim 1 wherein said aqueous medium of said standard solutions is deionized water and any contribution to said absorbance at wavelength x from the background of said water sample is deducted from said absorbance value of said water sample.

10. The method of claim 1 further including the step of adjusting the dosage of said corrosion inhibitor formulation for said aqueous system to provide the desired concentration of said corrosion inhibitor formulation in said aqueous system if said concentration of said corrosion inhibitor formulation in said sample is not said desired concentration.

11. The method of claim 1 wherein said scanning of said absorbance of said sample is conducted within 10 minutes of the time said sample is taken from said aqueous system.

12. A method for controlling the concentration of a water soluble corrosion inhibitor in the water of an aqueous system, comprising:
   obtaining a sample of water of an aqueous system to which has been added a water soluble corrosion inhibitor formulation that contains an active corrosion inhibitor component that has an absorption peak substantially centered about a wavelength x;

optionally removing oil and/or solids from said sample of water by decantation and/or filtration;

placing said sample of water from said aqueous system in a spectrophotometric cell of a scanning spectrophotometer;

scanning the absorbance of said sample along at least a segment of the ultraviolet wavelength range against a deionized water reference, wherein said scanned ultraviolet wavelength segment encompasses said wavelength x;

measuring the absorbance value of said sample at an absorbance peak centered about said wavelength x;

comparing said absorbance value of said sample to a standard curve comprising a plot of standard solutions having known concentrations of said corrosion inhibitor formulation in aqueous medium versus the absorbance values of said standard solutions at an absorbance peak centered about said wavelength x;

wherein said aqueous system is an oil field system in which water is a significant phase;

wherein said corrosion inhibitor formulation inhibits corrosion by the formation of an inhibitor film on surfaces of said aqueous system, wherein loss of residuals of said corrosion inhibitor formulation in said water of said aqueous system results in the desorption of said inhibitor film, whereby the concentration of said residuals of said formulated corrosion inhibitor in said sample is determined by correspondence of its said absorbance to a concentration on said standard curve; and adjusting the dosage of said corrosion inhibitor formulation for said aqueous system to provide the desired concentration of said residuals of said corrosion inhibitor formulation in said aqueous system if said concentration of said residuals of said corrosion inhibitor formulation in said sample is not said desired concentration.

13. The method of claim 12 wherein said corrosion inhibitor formulation contains a water soluble filming pyridine derivative component that has an absorption peak substantially centered at wavelength x.

14. The method of claim 12 wherein said water sample is filtered before it is placed in said scanning spectrophotometer.

15. The method of claim 12 wherein said corrosion inhibitor formulation contains a water soluble filming alkyl pyridine quaternary ammonium salt component that has an absorption peak substantially centered at wavelength x.

16. The method of claim 12 wherein said water sample contains from about 1 to about 20,000 ppm of said corrosion inhibitor formulation.

17. The method of claim 12 wherein said water sample contains from about 10 to about 200 ppm of said corrosion inhibitor formulation.

18. The method of claim 12 wherein said aqueous system is an oil field system.

19. The method of claim 12 wherein said aqueous medium of said standard solutions has an absorbance at wavelength x substantially commensurate to the background absorbance at wavelength x of said water sample.

20. The method of claim 12 wherein said aqueous medium of said standard solutions is deionized water and any contribution to said absorbance at wavelength x from the background of said water sample is deducted from said absorbance value of said water sample.

* * * * *